United States Patent [19]

Bradford et al.

[11] Patent Number: Plant 7,049

[45] Date of Patent: Oct. 24, 1989

[54] NECTARINE TREE (SUMMER BRIGHT)

[76] Inventors: Norman G. Bradford, 11875 E. Savana Rd.; Lowell G. Bradford, 12439 E. Savana Rd., both of Le Grand, Calif. 95333

[21] Appl. No.: 283,819

[22] Filed: Dec. 12, 1988

[51] Int. Cl.[4] ..... A01H 5/00

[52] U.S. Cl. ..... Plt./41

[58] Field of Search ..... Plt. 41

[56] References Cited

U.S. PATENT DOCUMENTS

P.P. 5,654 2/1986 Bradford ..... Plt. 41

*Primary Examiner*—James R. Feyrer

[57] ABSTRACT

The present invention relates to a nectarine tree and more particularly to a new and distinct variety broadly characterized by a medium size, medium vigor, hardy, very productive and regular bearing teee. The fruit matures under the ecological conditions described approximately the second week in July, with first picking on July 9, 1988. The fruit is uniformly large in size, clingstone in type, very firm making excellent quality for keeping and shipping, deep red over a reddish orange background in skin color, and both acidic and very sweet in flavor. The variety was developed as the result of a second generation seedling from the selected seed parent, Red Diamond (U.S. Pat. No. P.P. 3,165, and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Summer Bright". The present variety was hybridized in 1981 by us in a cultivated area of our experimental orchard at Bradford Farms near Le Grand, Calif. in Merced County (San Joaquin Valley). It was the result of a second generation seedling of Red Diamond (U.S. Pat. No. P.P. 3,165) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety most nearly resembles the fruit of Summer Diamond (U.S. Pat. No. P.P. 5,654) by being a nearly full red colored nectarine with excellent firmness, but is distinguished therefrom and an improvement thereon by harvesting 5 days earlier, by being a clingstone instead of a freestone, and by being much sweeter in flavor.

The present variety is similar to its selected seed grandparent, Red Diamond (U.S. Pat. No. P.P. 3,165), in fruit appearance by being a nearly full red colored nectarine with excellent firmness, but is distinguished therefrom by ripening 18 days later and by being a clingstone instead of a freestone.

DRAWING

The accompanying photograph shows the characteristics of the whole fruit in skin color and form, a characteristic fruit divided near its suture plane showing the flesh and pit cavity, a typical stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on July 14, 1988. All major color code designations are by reference to the Inter-Society Color Council, National Bureau of Standards. Common color names are also used occasionally.

TREE

Size: Medium.
Vigor: Medium.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Color.*—Grayish yellowish brown [80. gy.yBr].
- *Lenticels.*—Numerous. Color: Strong brown [55. s.Br]. Average Size: ⅛" to ⅜", [3.175–9.525 mm.].

Branches:
- *Size.*—Medium.
- *Texture.*—Medium.
- *Color.*—1st year wood — Topside: Dark pink [6. d.Pk] in sunlight. 1st year wood — Underside: Brilliant yellow green [116. brill.YG]. Older wood: Grayish brown [61. gy.Br].
- *Lenticels.*—Numerous, very small.

Leaves:
- *Size.*—Large. Average length: 6.0" [152.4 mm.]. Average width: 1 9/16" [39.69 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125. m.01G]. Ventral Surface: Moderate yellow green [120. m.YG].

*Margin.*—Finely serrate.
*Venation.*—Pinnately net veined.
*Petiole.*—Average Length: 7/16" [11.11 mm.]. Average Thickness: 1/16" [1.588 mm.].
*Glands.*—Numbers: 2 to 4 per leaf. Position: Some oppositely and some alternately positioned on petiole and base of blade. Size: Large. Form: Reniform. Color: Grayish pink [8. gy.Pk].
*Stipules.*—Numerous. Length: ¼" to ⅜" [6.350 mm. to 9.525 mm.].

Flower buds:
*Hardiness.*—Hardy.
*Size.*—Medium.
*Length.*—Medium.
*Form.*—Free.
*Surface.*—Pubescent.

Flowers:
*Blooming period.*—Medium, as compared with other varieties.
*Size.*—Small.
*Color.*—Light pink [4. 1.Pk].

FRUIT

Maturity when described: Hard ripe, July 14, 1988.
Date of first picking: July 9, 1988.
Date of last picking: July 24, 1988.
Size: Uniform, large.
*Average diameter axially.*—2½" [63.50 mm].
*Average transversely in suture plane:* 2⅜" [60.33 mm].
Form: Uniform, symmetrical, globose to slightly oblong.
*Longitudinal section form.*—Round to slightly oval.
*Transverse section through diameter.*—Round.
Suture: An inconspicuous shallow line extending from the base to slightly beyond the apex with a marked depression on both sides of the pistil point.
Ventral surface: Rounded along the suture with lipping on both sides toward the apex.
Lips: Equal.
Cavity: Flaring, elongated in the suture plane, suture showing on one side.
Base: Slightly truncate.
Apex: Depressed within the suture.
Pistil point: Negligible in length.
Stem: Medium.
*Average length.*—⅜" [9.525 mm.].
*Average width.*—3/16" [4.763 mm.].

Skin:
*Thickness.*—Medium.
*Texture.*—Tough.
*Tenacity.*—Tenacious to flesh.
*Tendency to crack.*—None observed as of yet.
*Color.*—Very deep red [14. v.deep R] over deep redish orange [36. deep r0] background.

Flesh:
*Color.*—Brilliant yellow [83. brill.Y] with deep red [13. deep R] streaking toward the stone.

*Surface of the pit cavity.*—Deep red [13. deep R].
*Amygdalin.*—Moderate.
*Juice.*—Abundant, rich.
*Texture.*—Extremely firm, fine, crisp.
*Fibers.*—Abundant, fine, tender.
*Ripens.*—Evenly.
*Flavor.*—Acidic with an abundance of sugar.
*Aroma.*—Moderate.
*Eating quality.*—Best.

STONE

Type: Clingstone.
Form: Oval.
Base: Straight.
Apex: Acute.
Sides: Equal.
Surface: Irregularly furrowed near the apex and pitted toward the base.
Ridges: Jagged.
Color: Light yellowish brown [76. 1.yBr].
Pit wall: 3/16" [4.763 mm.] thick.
Tendency to split: Very slight.
Kernel:
*Form.*—Oval.
*Taste.*—Sweet.
*Viable.*—Yes.
*Average width.*—7/16" [11.11 mm.].
*Average length.*—11/16" [17.46 mm.].
Pellicle color: Brownish pink [33. brPk].
Amygdalin: Scant.

USE

Market: Fresh and long distance shipping.
Keeping quality: Excellent.
Shipping quality: Excellent.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct mid-seasonal ripening variety of clingstone nectarine tree, substantially as illustrated and described, which most nearly resembles the Summer Diamond (U.S. Pat. No. P.P. 5,654) nectarine variety by producing fruit that is nearly full red in color and very firm in texture, but is distinguished from and an improvement on that variety by having fruit that ripens 5 days earlier, that is clingstone instead of freestone, and that is much sweeter in flavor, a valuable asset in today's marketplace.

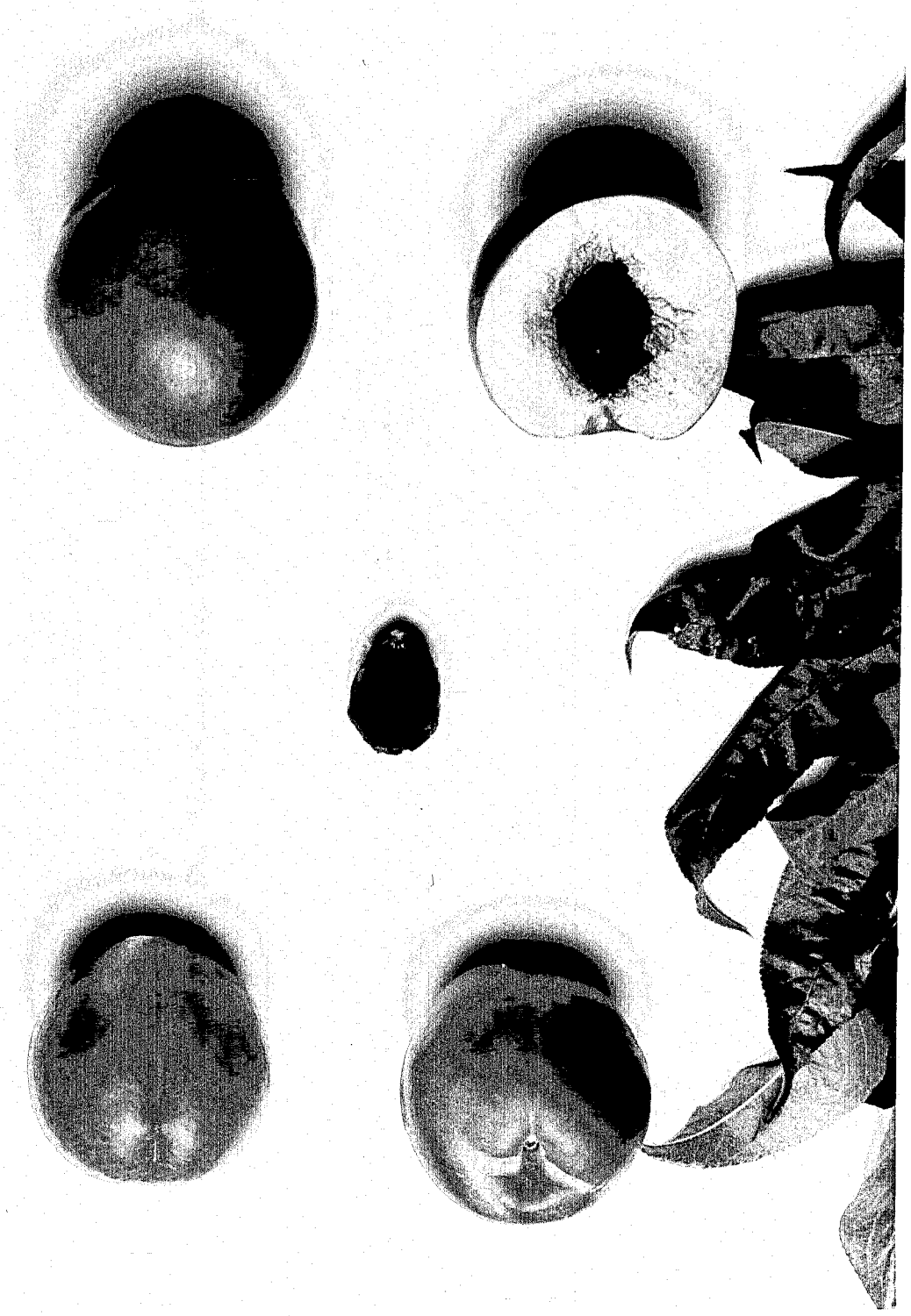

* * * * *